United States Patent
Swanson

(10) Patent No.: US 8,706,257 B2
(45) Date of Patent: Apr. 22, 2014

(54) CONNECTOR DESIGN FOR IMPLANTABLE PULSE GENERATOR FOR NEUROSTIMULATION, IMPLANTABLE STIMULATION LEAD, AND METHODS OF FABRICATION

(75) Inventor: John Swanson, Lake Oswego, OR (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 100 days.

(21) Appl. No.: 13/070,095

(22) Filed: Mar. 23, 2011

(65) Prior Publication Data

US 2012/0071951 A1    Mar. 22, 2012

Related U.S. Application Data

(60) Provisional application No. 61/316,548, filed on Mar. 23, 2010.

(51) Int. Cl.
*A61N 1/36* (2006.01)

(52) U.S. Cl.
USPC .......................................................... 607/72

(58) Field of Classification Search
None
See application file for complete search history.

(56) References Cited

U.S. PATENT DOCUMENTS

| | | | |
|---|---|---|---|
| 6,198,969 B1 | 3/2001 | Kuzma | |
| 6,321,126 B1 | 11/2001 | Kuzma | |
| 6,368,147 B1 | 4/2002 | Swanson | |
| 6,741,892 B1 | 5/2004 | Meadows et al. | |
| 7,003,351 B2 * | 2/2006 | Tvaska et al. | 607/37 |
| 7,047,077 B2 * | 5/2006 | Hansen et al. | 607/37 |
| 7,083,474 B1 | 8/2006 | Fleck et al. | |
| 7,590,451 B2 | 9/2009 | Tronnes et al. | |
| 2005/0027326 A1 | 2/2005 | Ries et al. | |
| 2005/0027338 A1 * | 2/2005 | Hill | 607/116 |
| 2005/0245982 A1 | 11/2005 | Kast et al. | |
| 2007/0067000 A1 * | 3/2007 | Strother et al. | 607/36 |
| 2007/0288076 A1 * | 12/2007 | Bulkes et al. | 607/116 |
| 2008/0004618 A1 | 1/2008 | Johnson et al. | |
| 2009/0247018 A1 | 10/2009 | Kast et al. | |
| 2009/0287287 A1 | 11/2009 | Bedenbaugh | |
| 2010/0114279 A1 | 5/2010 | Strandberg et al. | |

* cited by examiner

*Primary Examiner* — Brian T Gedeon
*Assistant Examiner* — Ankit Tejani

(57) ABSTRACT

In one embodiment, a stimulation system for generating and delivering electrical stimulation pulse to tissue of a patient, comprises: a pulse generator for generating electrical pulses, the pulse generator comprising a housing portion and a header portion with feedthroughs extending from the housing portion into the header portion; and a stimulation lead comprising a flex film component enclosed in a lead body of insulative material, the flex film component including a plurality of electrically isolated conductors extending along a substantial length of the stimulation lead, the stimulation lead further comprising a plurality of electrodes electrically coupled to the conductors, the flex film component comprising a proximal portion that is exposed out of the insulative material of the lead body and includes a plurality of terminal bond bands, the terminal bond bands being electrically coupled to the conductors; and wherein the header portion of the pulse generator comprises a lid component to compress the terminal bond pads of the stimulation lead into electrical contact with conductors of feedthroughs of the pulse generator.

14 Claims, 7 Drawing Sheets

CONNECTOR DESIGN FOR IMPLANTABLE PULSE GENERATOR FOR NEUROSTIMULATION, IMPLANTABLE STIMULATION LEAD, AND METHODS OF FABRICATION

CROSS-REFERENCE TO RELATED APPLICATIONS

This application claims the benefit of U.S. Provisional Application No. 61/316,548, filed Mar. 23, 2010, which is incorporated herein by reference.

TECHNICAL FIELD

This application is generally related to implantable neurostimulation systems and methods of fabrication thereof.

BACKGROUND

Neurostimulation systems are devices that generate electrical pulses and deliver the pulses to nerve tissue to treat a variety of disorders. Spinal cord stimulation (SCS) is the most common type of neurostimulation. In SCS, electrical pulses are delivered to nerve tissue in the spine typically for the purpose of chronic pain control. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue. Specifically, applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

SCS systems generally include a pulse generator and one or more leads. A stimulation lead includes a lead body of insulative material that encloses wire conductors. The distal end of the stimulation lead includes multiple electrodes that are electrically coupled to the wire conductors. The proximal end of the lead body includes multiple terminals, which are also electrically coupled to the wire conductors, that are adapted to receive electrical pulses. The distal end of a respective stimulation lead is implanted within the epidural space to deliver the electrical pulses to the appropriate nerve tissue within the spinal cord that corresponds to the dermatome(s) in which the patient experiences chronic pain. The stimulation leads are then tunneled to another location within the patient's body to be electrically connected with a pulse generator or, alternatively, to an "extension."

The pulse generator is typically implanted within a subcutaneous pocket created during the implantation procedure. In SCS, the subcutaneous pocket is typically disposed in a lower back region, although subclavicular implantations and lower abdominal implantations are commonly employed for other types of neuromodulation therapies.

The pulse generator is typically implemented using a metallic housing that encloses circuitry for generating the electrical pulses, control circuitry, communication circuitry, a rechargeable battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on a stimulation lead. Due to the requirements of conventional annular electrical connectors, the size of the header of conventional pulse generators is significant thereby imposing constraints upon the ability to reduce the size of conventionally-designed pulse generators.

SUMMARY

In one embodiment, a stimulation system for generating and delivering electrical stimulation pulse to tissue of a patient, comprises: a pulse generator for generating electrical pulses, the pulse generator comprising a housing portion and a header portion with feedthroughs extending from the housing portion into the header portion; and a stimulation lead comprising a flex film component enclosed in a lead body of insulative material, the flex film component including a plurality of electrically isolated conductors extending along a substantial length of the stimulation lead, the stimulation lead further comprising a plurality of electrodes electrically coupled to the conductors, the flex film component comprising a proximal portion that is exposed out of the insulative material of the lead body and includes a plurality of terminal bond bands, the terminal bond bands being electrically coupled to the conductors; and wherein the header portion of the pulse generator comprises a lid component to compress the terminal bond pads of the stimulation lead into electrical contact with conductors of feedthroughs of the pulse generator.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

DETAILED DESCRIPTION

Figure 1:
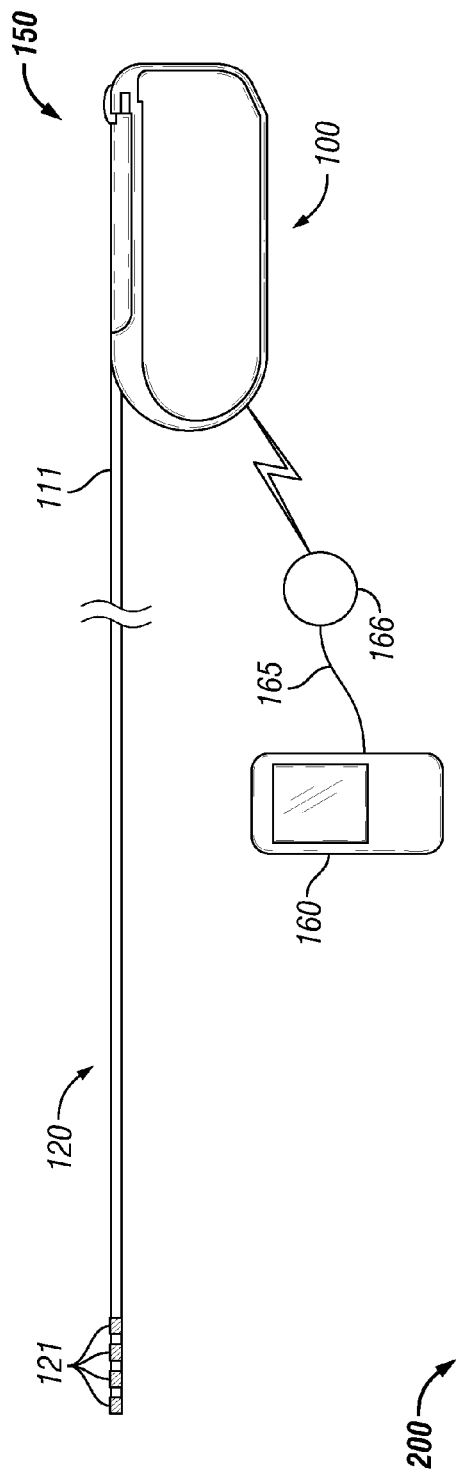
FIG. 1 depicts a stimulation system according to one representative embodiment.

FIG. 1 depicts stimulation system 150 that generates electrical pulses for application to tissue of a patient according to one embodiment. In one embodiment, system 150 is adapted to generate electrical pulses and deliver the pulses to tissue of the patient. For example, system 150 may be adapted to stimulate spinal cord tissue, peripheral nerve tissue, deep brain tissue, cortical tissue, cardiac tissue, digestive tissue, pelvic floor tissue, or any other suitable tissue within a patient's body.

System 150 includes implantable pulse generator 100 that is adapted to generate electrical pulses for application to tissue of a patient. Implantable pulse generator 100 typically comprises a metallic housing that encloses pulse generating circuitry, a controller, a charging coil, battery, far-field and/or near field communication circuitry, battery charging circuitry, etc. of the device. Although an implantable pulse generator is shown for the embodiment of FIG. 1, an external pulse generator (e.g., a "trial" stimulator) may alternatively be employed. The controller typically includes a microcontroller or other suitable processor for controlling the various other components of the device. Software code is typically stored in memory of the pulse generator 100 for execution by the microcontroller or processor to control the various components of the device.

A processor and associated charge control circuitry for an implantable pulse generator is described in U.S. Patent Publication No. 20060259098, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. patent Ser. No. 11/109,114, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 20060170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within pulse generator 100. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation system 150 further comprises one or more stimulation leads 120. Stimulation lead 120 comprises a lead body of insulative material about a plurality of conductors that extend from a proximal end of lead 120 to its distal end. The conductors electrically couple a plurality of electrodes 121 to a plurality of terminals (not shown in FIG. 1) of lead 120. The terminals are adapted to receive electrical pulses from pulse generator 100 or from an optional extension lead (not shown). In some embodiments, the terminals of lead 120 and the header of pulse generator 100 are adapted according to a high density connection design. Electrodes 121 of lead 120 are adapted to apply stimulation pulses to tissue of the patient. Only a few electrodes 121 are shown in FIG. 1, although any suitable number may be employed. In one embodiment, sixteen electrodes 121 are provided. Also, sensing of physiological signals may occur through electrodes 121, the conductors, and the terminals. Additionally or alternatively, various sensors (not shown) may be located near the distal end of stimulation lead 120 and electrically coupled to terminals through conductors within the lead body 111.

Figure 2C:
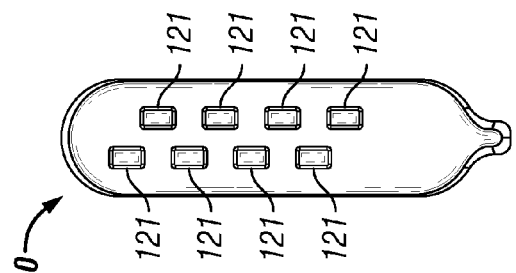
FIGS. 2A-2C depict respective electrode configurations that may be used in the system of FIG. 1 according to one representative embodiment.
Figure 2B:
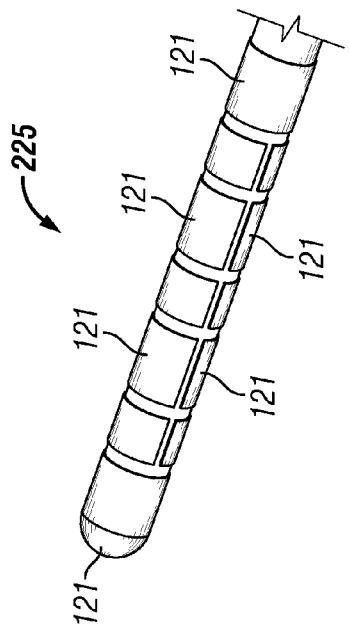
Figure 2A:
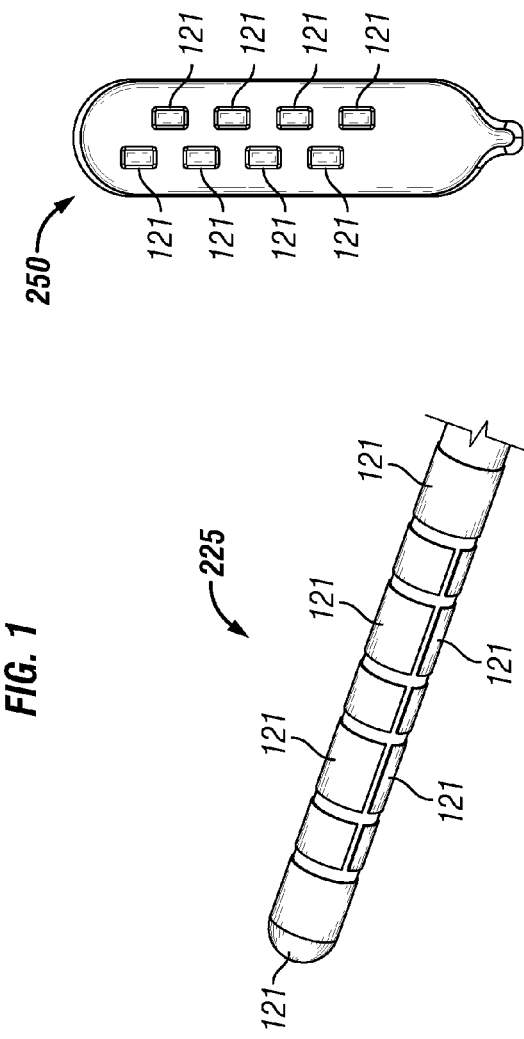

FIGS. 2A-2C respectively depict stimulation portions 200, 225, and 250 for inclusion at the distal end of lead 120. Stimulation portion 200 depicts a conventional stimulation portion of a "percutaneous" lead with multiple ring electrodes. Stimulation portion 225 depicts a stimulation portion including several "segmented electrodes." The term "segmented electrode" is distinguishable from the term "ring electrode." As used herein, the term "segmented electrode" refers to an electrode of a group of electrodes that are positioned at the same longitudinal location along the longitudinal axis of a lead and that are angularly positioned about the longitudinal axis so they do not overlap and are electrically isolated from one another. Example fabrication processes are disclosed in U.S. Provisional Patent Application Ser. No. 61/247,360, entitled, "METHOD OF FABRICATING STIMULATION LEAD FOR APPLYING ELECTRICAL STIMULATION TO TISSUE OF A PATIENT," which is incorporated herein by reference. Stimulation portion 250 includes multiple planar electrodes on a paddle structure.

Stimulation system 150 may optionally comprise an extension lead. Extension leads are adapted to connect between pulse generator 100 and stimulation lead 120. That is, electrical pulses are generated by pulse generator 100 and provided to the extension lead via a plurality of terminals on the proximal end of the extension lead. The terminals of the extension lead may be fabricated in the same manner as the terminals of lead 120 as described below. The electrical pulses are conducted through conductors within the lead body of the extension lead to a housing of the extension lead. The housing of the extension lead includes a plurality of electrical connectors, similar to the electrical connectors used in the header of the pulse generator 100, that are adapted to connect to the terminals of lead 120. Thereby, the pulses originating from pulse generator 100 and conducted through the extension lead are provided to stimulation lead 120. The pulses are then conducted through the conductors of lead 120 and applied to tissue of a patient via electrodes 121.

Controller device 160 may be implemented to recharge the battery of pulse generator 100 (although a separate recharging device could alternatively be employed). A "wand" 165 may be electrically connected to controller device through suitable electrical connectors (not shown). The electrical connectors are electrically connected to coil 166 (the "primary" coil) at the distal end of wand 165 through respective wires (not shown). Typically, coil 166 is connected to the wires through capacitors (not shown). Also, in some embodiments, wand 165 may comprise one or more temperature sensors for use during charging operations.

The patient then places the primary coil 166 against the patient's body immediately above the secondary coil (not shown), i.e., the coil of the implantable medical device. Preferably, the primary coil 166 and the secondary coil are aligned in a coaxial manner by the patient for efficiency of the coupling between the primary and secondary coils. Controller 160 generates an AC-signal to drive current through coil 166 of wand 165. Assuming that primary coil 166 and secondary coil are suitably positioned relative to each other, the secondary coil is disposed within the field generated by the current driven through primary coil 166. Current is then induced in the secondary coil. The current induced in the coil of the implantable pulse generator 100 is rectified and regulated to recharge the battery by the charging circuitry of pulse generator 100. The charging circuitry may also communicate status messages to controller 160 during charging operations using pulse-loading or any other suitable technique. For example, the controller of pulse generator 100 may communicate the coupling status, charging status, charge completion status, etc.

External controller device 160 is also a device that permits the operations of pulse generator 100 to be controlled by user after pulse generator 100 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with IPG 100.

Controller device 160 preferably provides one or more user interfaces to allow the user to operate pulse generator 100 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. IPG 100 modifies its internal parameters in response to the control signals from controller device 160 to vary the stimulation characteristics of stimulation pulses transmitted through stimulation lead 120 to the tissue of the patient. Neurostimulation systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference.

Figure 3:
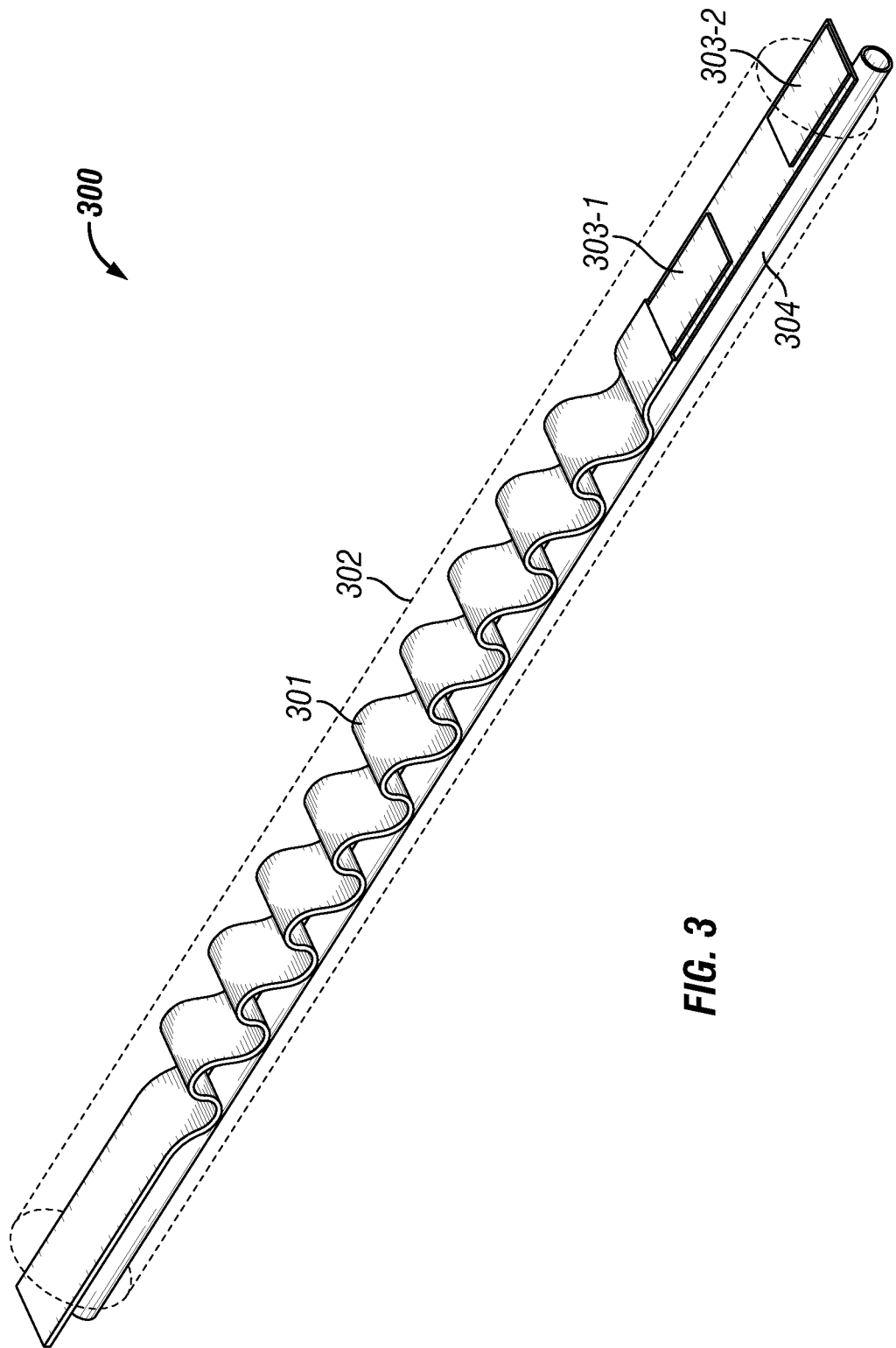
FIG. 3 depicts a flex film component for use in a stimulation lead according to one representative embodiment.

In some embodiments, stimulation lead 120 is fabricated using an internal flex film component. FIG. 3 depicts stimulation lead body 300 according to one representative embodiment. Stimulation lead body 300 comprises flex film component 301 within insulative material 302. Flex film component 301 includes a plurality of conductive traces sealed within the flex film material (e.g., liquid crystal polymer (LCP)).

In one embodiment, two layers of flex film are included within flex film component 301 and two respective sets 303-1 and 303-2 of conductive traces are provided. In this specific embodiment, eight conductive traces are provided for each layer within the LCP material. In one embodiment, each conductor trace is 50 microns wide and 18 microns thick. In a respective layer of flex film component 301, respective conductor traces are separated by a 50 micron pitch. The conductive traces extend along the length of lead body 300 for the purposes of conducting stimulating current along the length of lead body 300 between electrodes and terminals. The distal ends of the two sets 303-1 and 303-2 of conductive traces are shown to be exposed for the sake of illustration. Flex film component 301 may be fabricated using conventional processes. Although LCP is employed according to one representative embodiment, other suitable flexible polymer materials may be employed such as polyimide.

As shown in FIG. 3, flex film component 301 is provided with a serpentine configuration within lead body 300. That is, flex film component 301 is sinuous, bending "up" and "down" in respective curves repeatedly along the length of lead body 300. When a stretching force is applied to lead body 300, flex film component 301 is capable of elastic elongation. That is, lead body 300 will increase its length under the stretching force by reducing the curvature in the bends of flex film component 301. When the stretching force is removed, flex film component 301 returns to its prior configuration. The sinuous or serpentine configuration of flex film component 301 may be obtained using the various heated gear arrangements as disclosed in U.S. patent application Ser. No. 13/070,055, entitled "STIMULATION LEAD COMPRISING INTERNAL FLEX FILM COMPONENT AND METHOD OF FABRICATION," which is incorporated herein by reference.

Further as shown in FIG. 3, stimulation lead body 300 comprises elastic tube 304. Elastic tube 304 preferably provides a low friction surface to ease insertion and removal of a stiffening/steering stylet through lead body 300. In one embodiment, elastic tube 304 possesses an inner diameter of approximately 0.020 inches. Also, elastic tube 304 is adapted to flex and elongate. A suitable material for elastic tube 304 is CARBOSIL™ (a silicone polycarbonate urethane).

Insulative material 302, surrounding flex film component 301 and elastic tube 304, is likewise capable of elastic elongation by suitably selecting material characteristics of material 302. A relatively low durometer may be selected for material 302, for example, at approximately or below a durometer of 40 shore A.

Fabrication of stimulation lead body 300 may occur using different combinations of processing steps. In some embodiments, the process begins by fabricating elastic tube 304. In one embodiment, a TEFLON™ (a fluoropolymer of tetrafluoroethylene) coated mandrel is coated with suitable elastic, biocompatible insulative material. The coated-mandrel is cut to length. A length of flex film component 301 with embedded conductive traces is fabricated. Any suitable length may be employed for tube 304 and flex film component 301. For example, in one embodiment, tube 304 and flex film component 301 in their non-stretched or relaxed states are fabricated to be approximately 30 cm. When component 301 is adapted to include multiple layers, the layers are fabricated in a "stair-stepped" manner at the ends of component 301 to facilitate access to each layer. The medial portion of flex film component 301 is fabricated or post-fabrication processed to repeatedly bend back and forth along the length of component 301 while the respective ends of flex film component 301 are preferably left substantially flat.

Upon fabrication of these components, flex film component 301 and tube 304 are adhered together. Insulative material 302 is provided over the assembly of flex film component 301 and tube 304. Any suitable process may be employed to provide insulative material 302 including dip-coating, spraying, over-molding, etc. Centerless grinding or other mechanical processing may be applied to obtain a substantially uniform outer diameter. In one embodiment, an outer diameter of lead body 300 of 0.060 inches is obtained, although any suitable diameter may be selected.

By fabricating lead body 300 in the discussed manner, lead body 300 is capable of elastic elongation under relatively low stretching forces. Also, after removal of the stretching force, lead body 300 is capable of resuming its original length and profile. For example, lead body 300 may stretch 10%, 20%, 25%, 35%, or even up or above to 50% at forces of about 0.5, 1.0, and/or 2.0 pounds of stretching force. The ability to elongate at relatively low forces may present one or more advantages for implantation in a patient. For example, as a patient changes posture (e.g., "bends" the patient's back), the distance from the implanted pulse generator to the stimulation target location changes. Lead body 300 may elongate in response to such changes in posture without damaging the conductors of lead body 300 or disconnecting from pulse generator. Also, deep brain stimulation implants, cortical stimulation implants, and occipital subcutaneous stimulation implants usually involve tunneling of the lead body through tissue of the patient's neck to a location below the clavicle. Movement of the patient's neck subjects a stimulation lead to significant flexing and twisting which may damage the conductors of the lead body. Due to the ability to elastically elongate, lead body 300 is better adapted for such implants than some other lead body designs.

After fabrication of lead body 300, electrodes are provided on lead body 300. The respective layers of flex film component 301 are preferably arranged to facilitate electrode and terminal fabrication. As shown in FIG. 3, the second set 303-2 of conductive traces of the "lower" layer of flex film component 301 extends beyond the first set 303-1 of conductive traces of the "upper" layer of flex film component 301. Thereby, the second set 303-2 of conductive traces are readily accessible for subsequent electrical connection with other electrical components.

Figure 4:
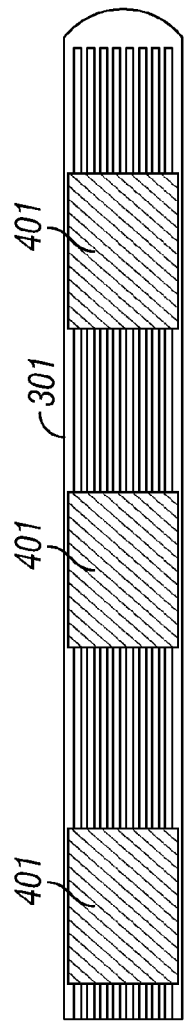
FIG. 4 depicts a segment of a flex film component including bond pad terminals according to one representative embodiment.

Further, in one embodiment, as shown in isolation in FIG. 4, a respective bond or connection pad 401 is fabricated on the upper surface of flex film component 301. Each pad 401 is electrically connected to one of the electrical traces of sets 303-1 and 303-2 of traces.

Figure 5:
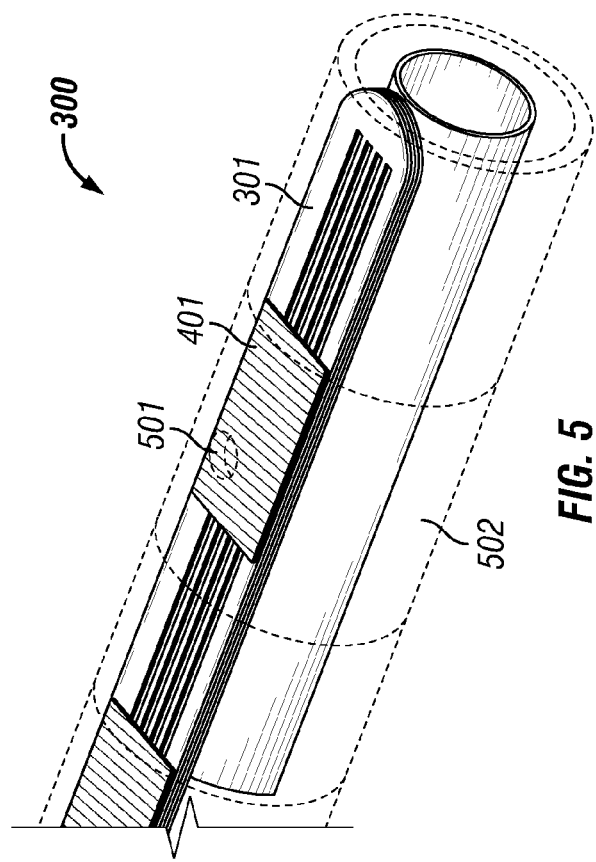
FIG. 5 depicts electrodes on a distal end of a stimulation lead body according to one representative embodiment.

FIG. 5 depicts provision of one electrode at the distal end of lead body 300. As shown in FIG. 5, via 501 is provided to electrically connect to one of the bond pads 401. A suitable laser may be employed to ablate insulative material 302 of lead body to expose the respective bond pad 401. Conductive material is provided within the created aperture to form via 501. Electrode 502 is provided in electrical contact with via 501.

A number of suitable techniques may be employed for this process (see electrode attachment techniques disclosed in U.S. Pat. No. 7,039,470, entitled "Medical lead and method for medical lead manufacture," which is incorporated herein by reference). Crimping or swaging of the conductive band may be employed to place the conductive band about the lead body. In one embodiment, a jumper wire is optionally utilized to connect to bond pad 401 through an aperture in lead body 300. The jumper wire is welded to the conductive band placed about the lead body 300.

In one embodiment, electrode 502 is fabricated using a liquid dispensing process. For example, a conductive polymer in a suitable solvent may be disposed about the circumference of lead body 300. During the dispensing process, the conductive polymer fills the aperture in lead body 300 and forms a conductive ring at the appropriate axial position along lead body 300. After application of the conductive polymer, plating of conductive material (e.g., platinum) may also be employed to form electrode 502. Also, another conductive polymer material (e.g., a PEDOT-based conductive polymer material) may be employed over the initial dispensed material.

In other embodiments, a paddle style distal end with an array of electrodes may be provided. Each electrode may be electrically coupled to a respective conductive trace of flex film component 301 through a respective bond pad 401 and a respective jumper wire. In another embodiment, segmented electrodes may be fabricated in lieu of circumferential electrodes.

Figure 6:
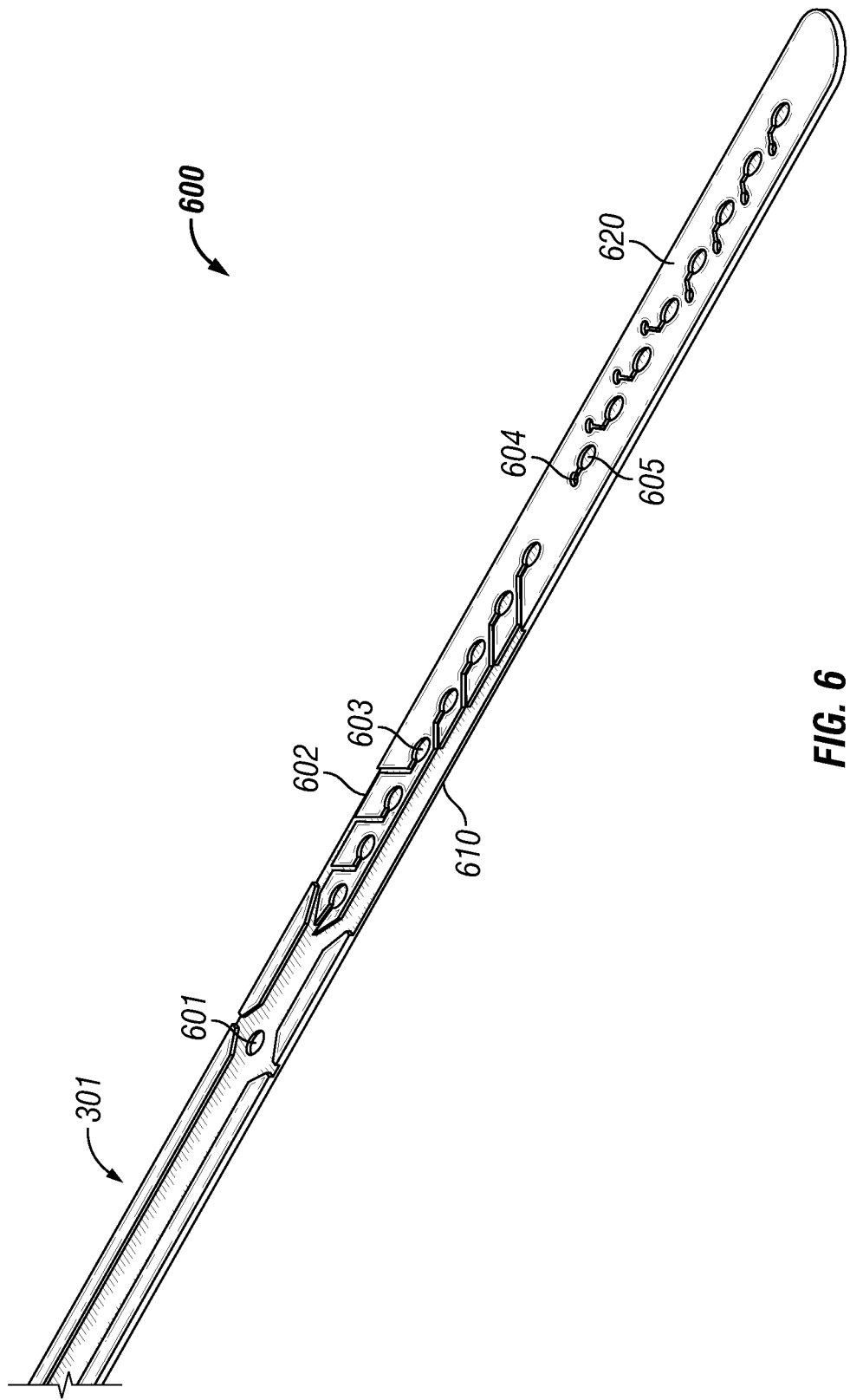
FIG. 6 depicts a proximal or connector end of a flex film component for a stimulation lead according to one representative embodiment.

FIG. 6 depicts proximal end 600 of flex film component 301 according to one representative embodiment. Flex film component 301 provides a connection design for connecting with the header of pulse generator 100 in an efficient manner. When the lead body is formed using suitable molding or other techniques, proximal end 600 is preferably left exposed and is not encapsulated by the insulative material. Thereby, proximal end 600 may directly connect with the electrical connectors of the header of pulse generator 100.

As shown in FIG. 6, proximal end 600 of flex film component 301 comprises two sets of terminals 610 and 620. The two sets 610 and 620 of terminals are respectively electrically connected to the two respective sets 303-1 and 303-2 of conductive traces. The terminals are fabricated in the form of connector bond pads. The respective terminals can be directly connected to the electrical traces. Alternatively, vias can be employed to connect to the electrical traces. As shown in FIG. 4, the bond pad terminals (including terminal 603) of the first set are electrically connected to respective traces (including trace 602) and the bond pad terminals (including terminal 605) of the second set are electrically connected to internal traces through respective vias (including via 604). The spacing and arrangement of terminals on proximal end 600 corresponds to the spacing and arrangement of electrical connectors within the header of pulse generator 100. Proximal end 600 of flex film component 301 also comprises aperture 601 for locking component 301 to pulse generator 100. In some embodiments, the terminals may be fabricated the fabrication process employed for fabricate contacts on a medical probe as disclosed in U.S. Pat. No. 6,368,147, which is incorporated herein by reference. Such a process may permit each contact to be independently suspended above or on the polymer substrate to facilitate electrical contact with the pulse generator.

Figure 7:
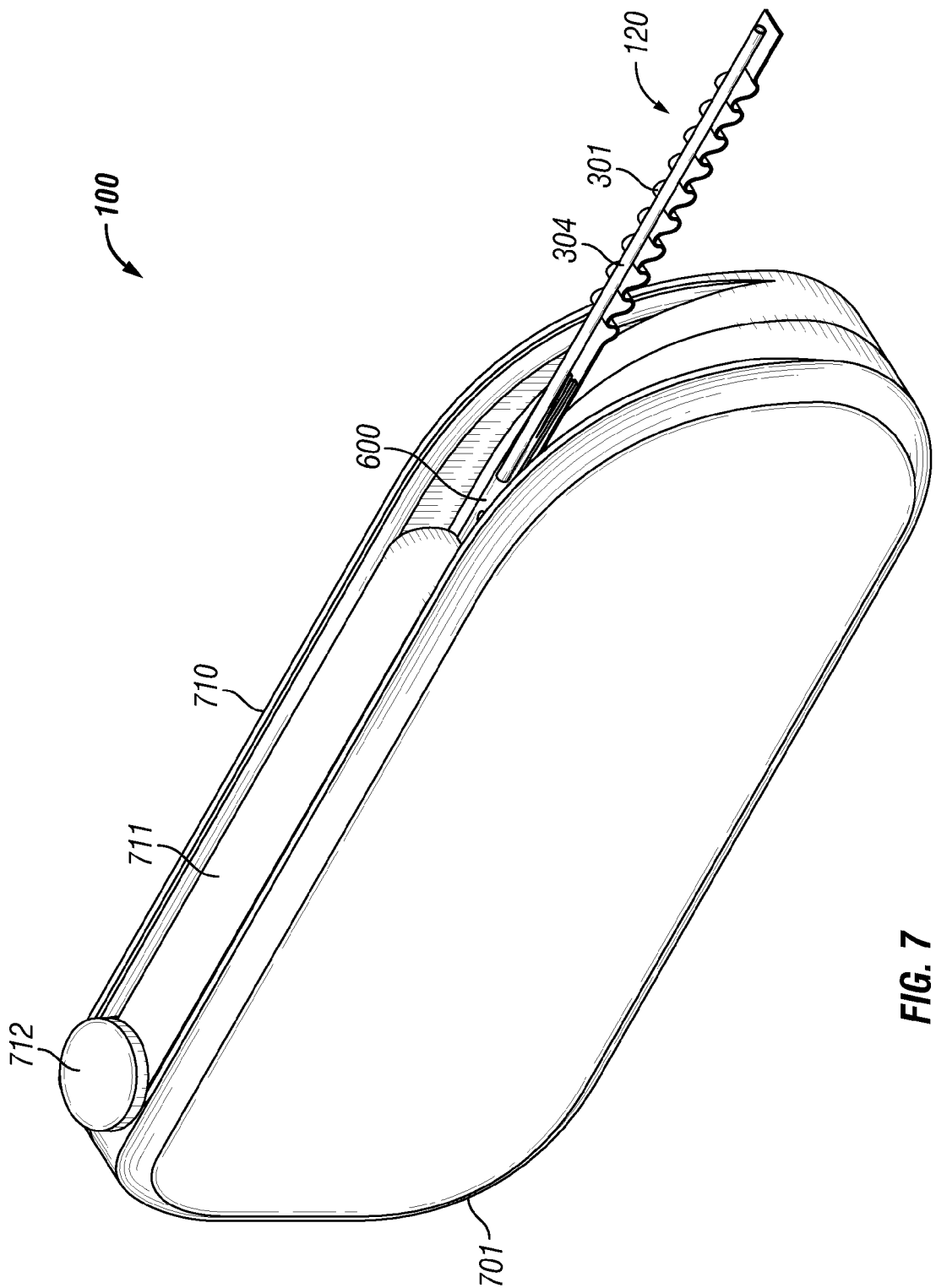
FIG. 7 depicts a pulse generator including a header adapted to connect with the proximal end shown in FIG. 6 according to one representative embodiment.

FIG. 7 depicts implantable pulse generator 100 adapted to electrically connect with proximal end 600 of lead 120 (the insulative lead body of lead 120 is not shown in FIG. 7 to permit the view of the internal components of lead 120) according to one representative embodiment. Pulse generator 100 comprises hermetically sealed housing 701. The battery, controller, recharging circuitry, pulse generating circuitry, etc. are contained within housing 701. The pulse generating circuitry is electrically connected, through switching circuitry, to "feedthrough" wires (not shown) which are known in the art. The wires of the feedthroughs extend through the ceramic material into header 710 of pulse generator 100. Although not required for all embodiments, selected embodiments reduce the cost and complexity of the header design using direct contact of the terminal portion of the stimulation lead with feedthrough conductors.

Figure 10:
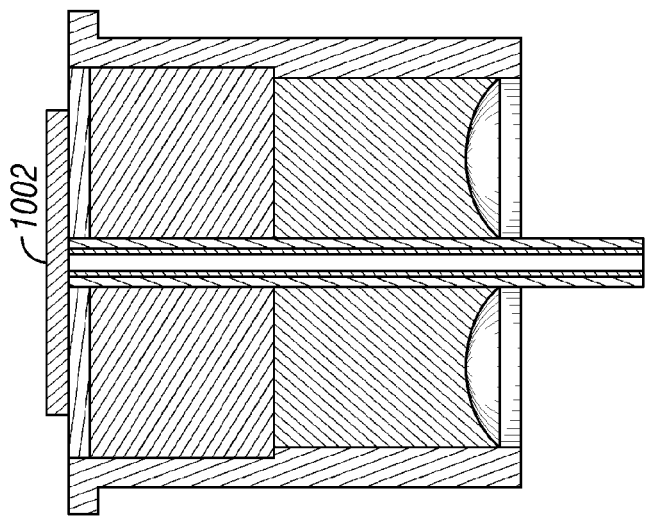
FIG. 10 depicts a feedthrough that may be employed within a header of an implantable pulse generator according to one representative embodiment.

Header 710 comprises compression lid 711. Lid 711 is mechanically coupled to hinge and seal component 712. In one specific embodiment, a separate hinge pin is not required wherein a portion of the seal, itself, is adapted to function as a hinging mechanism where the flexible compliant material retains the other components together. Also, a hard stop may be employed in conjunction with the hinge and seal component 712. Lid 711 may be pivoted between an open position and a closed position (shown in FIG. 7). In the open position, the surgeon may place proximal end 600 of stimulation lead 120 on the electrical connectors of header 710. In the closed position, lid 711 compresses the terminals of proximal end 600 against the electrical connectors of header 710. In one embodiment, the terminals are placed in direct contact with the feedthrough wires or pins. In another embodiment, each terminal is placed into contact with a conductive pad 1002 on the top of a corresponding feedthrough (see FIG. 10) in header 710. Referring again to FIG. 7, in the closed position, lid 711 also seals proximal end 600 within header 710 to prevent bodily fluids, after implantation, from shorting the electrical connections between the terminals and electrical connectors of header 710. Although, in one embodiment, seal component 712 contains a hinging mechanism, lid 711 may be additionally or alternatively locked into place using a pin, clip, set screw, or other suitable mechanism (not shown).

Figure 8:
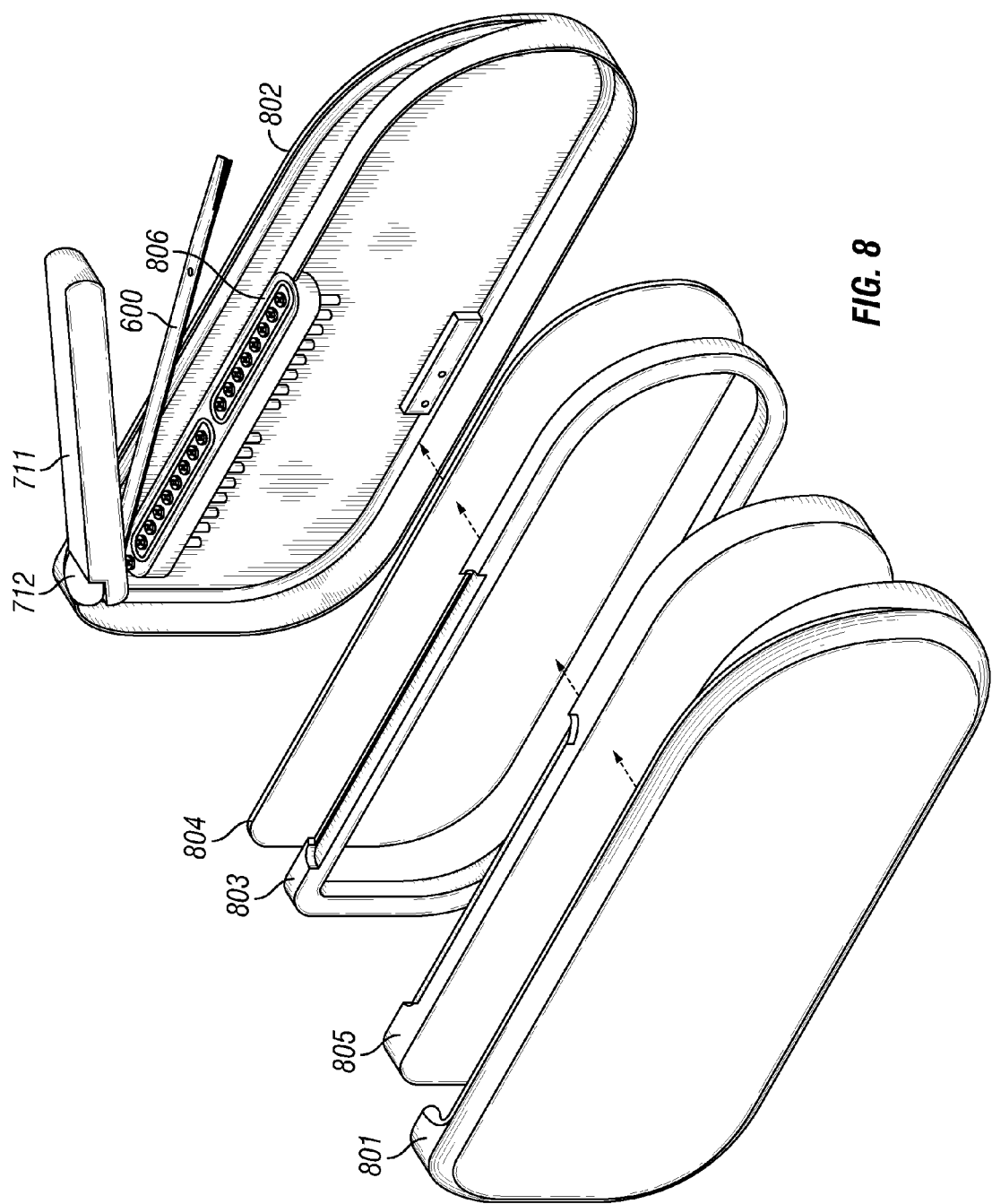
FIG. 8 depicts an exploded view of the implantable pulse generator shown in FIG. 7 according to one representative embodiment.

FIG. 8 depicts an exploded view of pulse generator 100. As shown in FIG. 8, pulse generator 100 is assembled using two housing components 801 and 802. The active components of pulse generator 100 are disposed within these housing components 801 and 802. One or more circuit board components 805 and battery 804 are held in place with one or more frame components 803. Housing components 801 and 802 are welded together enclosing these components and with feedthrough assembly 806 disposed to protrude into the subsequently provided header portion. When welded together, housing components 801 and 802 form the "can" as is known in the art.

Feedthrough assembly 806 comprises a plurality of feedthrough components. Each feedthrough component of assembly 806 comprises a metal ferrule, ceramic or other suitable insulating material about a feedthrough wire. In one embodiment, the feedthrough components are arranged with a pitch of 0.050 inches between respective wires. Each feedthrough wire extends from the interior of the can into the header portion of pulse generator 100. The portions of the feedthrough wires, internal to the can, are electrically coupled to the pulse output pads, pins, traces, other electrical outputs from board components 805 (which carry the output stimulation pulses). On the header side, the feedthrough wires are preferably machined or ground to a specific height. In one embodiment, the feedthrough wires or other conductors of the feedthroughs are directly electrically connected to the terminals of lead 120. In one embodiment, a low durometer polymer film (e.g., of silicone) is attached to the substrate portion of feedthrough assembly around the individual feedthrough components. The low durometer polymer film acts as a connector fluid seal and isolation component.

Figure 9:
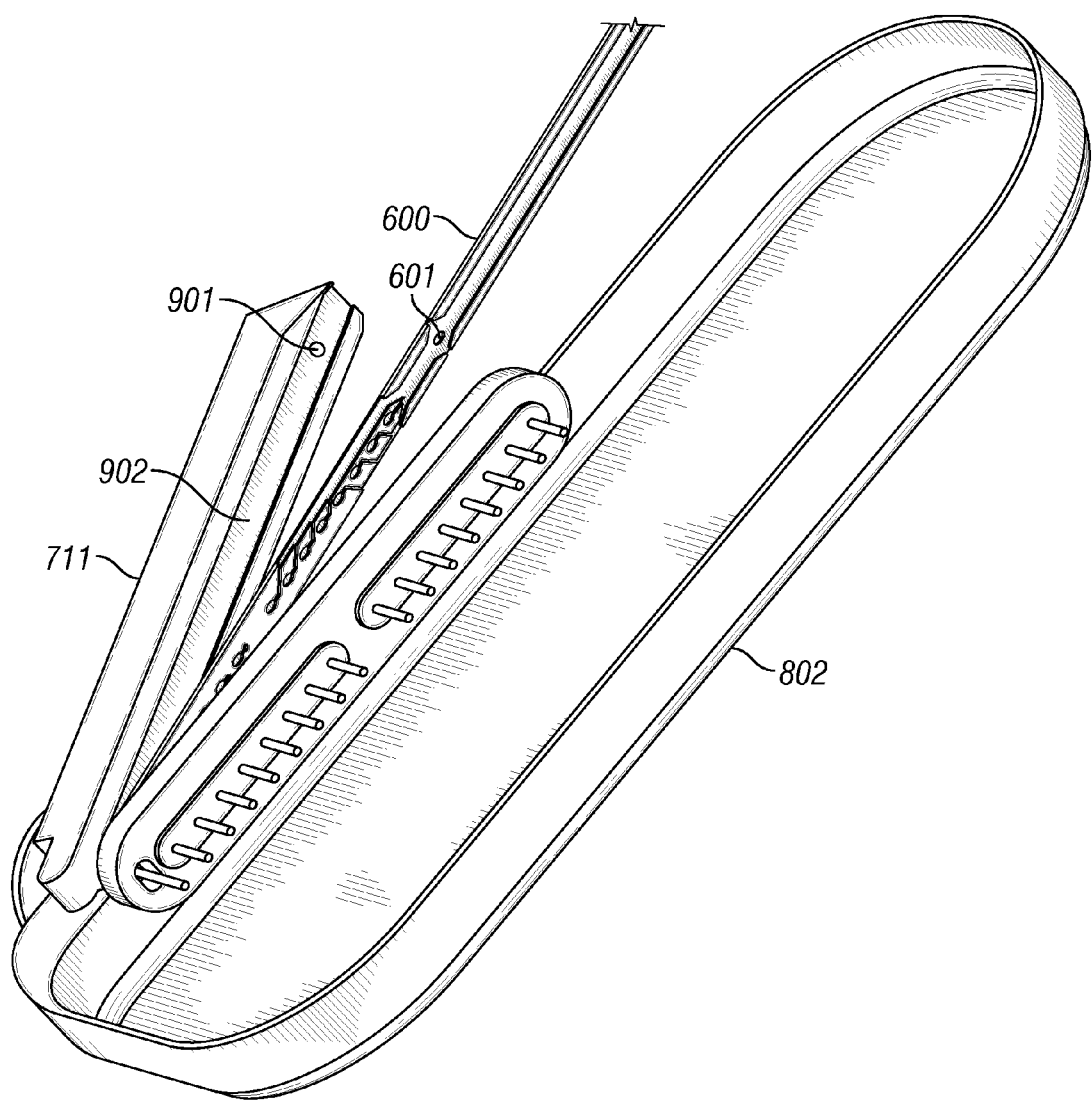
FIG. 9 depicts an underneath view of a portion of the implantable pulse generator shown in FIG. 7 according to one representative embodiment.

FIG. 9 depicts an "underneath" view of housing component with the header and lead 120. Lid 711 comprises a small depression corresponding to the shape of proximal end 600 of flex film component 301. Within the depression, lid 711 comprises pin 901 and lid insert 902. Insert 902 preferably comprises a low durometer layer that may be backed with polyether ether ketone (PEEK) or LCP to provide mechanical robustness and provide flex relief. Alternatively, lid 711 may be fabricated from a metal alloy or material. When lid 711 is placed into the closed position, pin 901 of lid 711 is disposed through aperture 601 thereby holding proximal end 600 of flex film component 301 in place. A pin may be alternatively placed on the housing in lieu of on the lid 711. Further, lid 711 compresses the bond pad terminals of proximal end 600 against the feedthrough wires or other conductors of feedthrough assembly 806. The bond pad terminals and such wires or conductors are thereby placed in electrical contact.

The design of header 710 and of proximal end 600 of flex film component 301 enables an efficient use of space for the electrical connection between pulse generator 100 and lead 120. The efficient use of space enables a reduction in size of pulse generator 100 relative to conventionally designed pulse generators for some embodiments. Further, the fabrication of systems components may be simplified for some embodiments.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

The invention claimed is:

1. A stimulation system for generating and delivering electrical stimulation pulse to tissue of a patient, comprising:
   a pulse generator for generating electrical pulses, the pulse generator comprising a housing portion and a header portion with feedthroughs extending from the housing portion into the header portion; and
   a stimulation lead comprising a flex film component enclosed in a lead body of insulative material, the flex film component comprising a substrate structure of flexible polymer material, the flex film component including a plurality of electrically isolated conductors extending along a majority of a length of the stimulation lead, the plurality of isolated conductors are sealed within the substrate structure and disposed in a substantially coplanar and parallel configuration within the substrate structure, the stimulation lead further comprising a plurality of electrodes electrically coupled to the electrically isolated conductors, the flex film component comprising a proximal portion of the substrate structure that is exposed out of the insulative material of the lead body and includes a plurality of terminal bond pads, the terminal bond pads being electrically coupled to the electrically isolated conductors; and
   wherein the header portion of the pulse generator comprises a lid component to compress the plurality of terminal bond pads of the stimulation lead into electrical contact with conductors of the feedthroughs of the pulse generator.

2. The stimulation system of claim 1 wherein the lid is attached at the header portion with a hinging mechanism and wherein the lid comprises a hard stop and a seal.

3. The stimulation system of claim 1 wherein the lid comprises an insert to contact the proximal portion of the flex film component, wherein the insert comprises an outer polymer layer and an interior polymer layer, wherein the outer polymer layer comprises a lower durometer than the interior polymer layer.

4. The stimulation system of claim 1 wherein the lid or the housing further comprises a pin and the proximal portion of the stimulation lead comprises an aperture, wherein when the lid is closed over the proximal portion, the pin is disposed through the aperture and secures the stimulation lead against removal by stretching forces placed on the stimulation lead.

5. The stimulation system of claim 1 wherein the header portion is adapted to compress the terminal bond pads against the feedthroughs.

6. The stimulation system of claim 1 wherein each of the feedthroughs comprises a conductive pad disposed on top of the respective feedthrough within the header portion for electrical contact with a corresponding terminal bond pad of the plurality of terminal bond pads of the proximal portion of the stimulation lead.

7. The stimulation system of claim 1 wherein the flex film component comprises a plurality of bends along a majority of a length of the stimulation lead.

8. The stimulation system of claim 7 wherein the stimulation lead is adapted to elastically elongate under application of stretching forces to the lead body without disconnection of electrical connections between the plurality of electrodes and the plurality of terminal bond pads through the conductors of the flex film component.

9. The stimulation system of claim 8 wherein the stimulation lead is capable of elongating more than 20% under a stretching force of less than 3 lbs.

10. The stimulation system of claim 8 wherein the stimulation lead is capable of elongating more than 20% under a stretching force of less than 0.5 lbs.

11. The stimulation system of claim 8 wherein the stimulation lead is capable of elongating more than 50% without damaging the electrically isolated conductors of the flex film component.

12. The stimulation system of claim 1 wherein the flex film component comprises a plurality of conductive pads and wherein the stimulation lead further comprises a plurality of vias, disposed underneath the plurality of electrodes, electrically connected with the plurality of conductive pads.

13. The stimulation system of claim 1 further comprising:
a stylet tube within the insulative material of the lead body, the stylet tube is adapted to elastically elongate under application of stretching forces to the lead body.

14. The stimulation system of claim 1 wherein the conductors of feedthroughs are feedthrough pins and the feedthrough pins are placed into direct electrical contact with terminal bond pads of the plurality of terminal bond pads of the stimulation lead.

* * * * *